United States Patent
Hess et al.

(10) Patent No.: US 7,732,214 B2
(45) Date of Patent: Jun. 8, 2010

(54) DIFFERENTIATION OF ACUTE AND CHRONIC MYOCARDIAL NECROSIS IN SYMPTOMATIC PATIENTS

(75) Inventors: Georg Hess, Mainz (DE); Andrea Horsch, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/212,037

(22) Filed: Sep. 17, 2008

(65) Prior Publication Data

US 2009/0087918 A1    Apr. 2, 2009

Related U.S. Application Data

(63) Continuation of application No. PCT/EP2007/052704, filed on Mar. 21, 2007.

(30) Foreign Application Priority Data

Mar. 24, 2006    (EP)    .................... 06111716

(51) Int. Cl.
*G01N 33/68* (2006.01)
(52) U.S. Cl. ................. 436/86; 436/63; 514/2
(58) Field of Classification Search ............ 436/63, 436/86; 422/61, 68.1; 514/2
See application file for complete search history.

(56) References Cited

U.S. PATENT DOCUMENTS

| | | | |
|---|---|---|---|
| 5,744,305 | A | 4/1998 | Fodor et al. |
| 6,461,828 | B1 | 10/2002 | Stanton et al. |
| 2003/0022235 | A1 | 1/2003 | Dahlen et al. |
| 2003/0109420 | A1* | 6/2003 | Valkirs et al. .......... 514/2 |
| 2004/0096988 | A1 | 5/2004 | Kang et al. |
| 2004/0121343 | A1* | 6/2004 | Buechler et al. ........ 435/6 |
| 2006/0008829 | A1* | 1/2006 | Hess et al. ............. 435/6 |
| 2009/0042228 | A1* | 2/2009 | Hess et al. ............ 435/17 |

FOREIGN PATENT DOCUMENTS

| | | |
|---|---|---|
| EP | 0648228 B1 | 11/1998 |
| WO | 02083913 A1 | 10/2002 |
| WO | 02089657 A2 | 11/2002 |

OTHER PUBLICATIONS

Sabatine et al. Circulation, vol. 105, 2002, pp. 1760-1763.*

Anderson, P. et al., "Molecular Basis of Human Cardiac Troponin T Isoforms Expressed in the Developing. Adult. and Failing Heart," Circulation Research 76:4 (Apr. 1995) 681-686.
Bonow. R., "New Insights Into the Cardiac Natriuretic Peptides," Circulation 93:11 (Jun. 1, 1996) 1946-1950.
Ferrieres, G. et al.. "Human cardiac troponin I: precise identification of antigenic epitopes and prediction of secondary structure," Clinical Chemistry 44:3 (1998) 487-493.
Ikran, H. et al., "An Ovine Model of Acute Myocardial Infarction and Chronic Left Ventricular Dysfunction," Angiology. The Journal of Vascular Diseases 48:8 (Aug. 1997) 679-688.
Ishii, J. et al., "Risk Stratification Using a Combination of Cardiac Troponin T and Brain Natriuretic Peptide in Patients Hospitalized for Worsening Chronic Heart Failure." The American Journal of Cardiology 89 (Mar. 15, 2002) 691-695.
Karl, J. et al., "Development of a novel, N-Terminal-pro BNP (NT-proBNP) assay with a low detection limit," Scand J Clin Lab Invest 59:Suppl 230 (1999) 177-181.
Lindahl, B. et al., "Serial Analyses of N-Terminal Pro-B-Type Natriuretic Peptide in Patients With Non-ST-Segment Elevation Acute Coronary Syndromes," Journal of the American College of Cardiology 45:4 (2005) 533-541.
Mueller, T. et al., "Lont-term stability of endogenous B-type natriuretic peptide (BNP) and amino terminal proBNP (NT-proBNP) in frozen plasma samples," Clin Chem Lab Med 42:8 (2004) 942-944.
Nolan, J. et al., "Suspension array technology: evolution of the flat array paradigm," Trends in Biotechnology 20:1 (Jan. 2002) 9-12.
Smith, M. et al., "Delayed metabolism of human brain natriuretic peptide reflects resistance to neutral endopeptidase," Journal of Endocrinology 167 (2000) 239-246.
Wu, A. et al., "Analytical and Clinical Evaluation of the Bayer ADVIA Centaur Automated B-Type Natriuretic Peptide Assay in Patients with Heart Failure: A Multisite Study," Clinical Chemistry 50:5 (2004) 867-873.
Yeo, K. et al., "Multicenter evaluation of the Roche NT-proBNP assay and comparison to the Biosite Triage BNP assay," Clinica Chimica Acta 338 (2003) 107-115.
"Myocardial Infarction Redefined—A Consensus Document of the Joint European Society of Cardiology/American College of Cardiology Committee for the Redfinition of Myocardial Infarction." JACC 36:3 (2000)959-969.

* cited by examiner

*Primary Examiner*—Maureen M Wallenhorst
(74) *Attorney, Agent, or Firm*—Marilyn Amick; Roche Diagnostics Operations, Inc.

(57) ABSTRACT

The present invention provides methods for diagnosing an acute cardiovascular event and for differentiating between an acute cardiovascular event and chronic heart failure based on measuring a cardiac troponin and a natriuretic peptide in a sample from a patient and comparing the measured amounts with reference amounts, as well as devices and kits for carrying out such methods.

12 Claims, No Drawings

DIFFERENTIATION OF ACUTE AND CHRONIC MYOCARDIAL NECROSIS IN SYMPTOMATIC PATIENTS

RELATED APPLICATIONS

This application is a continuation of PCT/EP2007/052704 filed Mar. 21, 2007 which claims priority to EP 06111716.4 filed Mar. 24, 2006.

FIELD OF THE INVENTION

The present invention relates to a method for diagnosing an acute cardiovascular event comprising the steps of determining the amount of a cardiac troponin in a sample of a subject, determining the amount of a natriuretic peptide in a sample of said subject, and diagnosing an acute cardiovascular event by comparing the amounts determined in the previous steps with reference amounts. Moreover, the present invention encompasses a method for differentiating between an acute cardiovascular event and chronic heart failure comprising the steps of determining the amount of a cardiac troponin in a sample of a subject, determining the amount of a natriuretic peptide in a sample of said subject, and differentiating between an acute cardiovascular event and chronic heart failure by comparing the amounts determined in the previous steps with reference amounts. Also comprised by the present invention are devices and kits for carrying out such methods.

BACKGROUND OF THE INVENTION

An aim of modern medicine is to provide personalized or individualized treatment regimens. These are treatment regimens which take into account a patient's individual needs or risks. A particularly important risk is the presence of a cardiovascular complication, particularly an unrecognized cardiovascular complication or a prevalence for such cardiovascular complications. Cardiovascular complications, particularly heart diseases, are the leading cause of morbidity and mortality in the Western hemisphere. Cardiovascular complications can remain asymptomatic for long periods of time. Therefore, reliable differential diagnosis of the presence of a cardiovascular complication is more difficult and error-prone than generally believed.

Specifically, patients suffering from symptoms of an acute cardiovascular event (e.g., myocardial infarction) such as chest pain are currently subjected to a troponin T-based diagnosis. To this end, troponin T levels of the patients are determined. If the amount of troponin T in the blood is elevated, i.e., above 0.1 ng/ml, an acute cardiovascular event is assumed and the patent is treated accordingly.

However, by using the current troponin T test, a significant portion of patients is false positively diagnosed as suffering from an acute cardiovascular event. It is to be understood that the subsequent therapy is less effective or even ineffective, resulting in more severe complications or even death.

Therefore, there is a clear long-standing need for means and methods allowing for a precise differential diagnosis of acute cardiovascular events. The said means and methods shall allow a reliable and efficient differential diagnosis and shall avoid the drawbacks of the current techniques.

Thus, the technical problem underlying the present invention must be seen as the provision of means and methods for complying with the aforementioned needs.

The technical problem is solved by the embodiments characterized in the claims and herein below.

SUMMARY OF THE INVENTION

Accordingly, the present invention relates to a method for diagnosing an acute cardiovascular event comprising the steps of:
a) determining the amount of a cardiac troponin in a sample of a subject,
b) determining the amount of a natriuretic peptide in a sample of said subject, and
c) diagnosing an acute cardiovascular event by comparing the amounts determined in steps a) and b) with reference amounts.

The method of the present invention, preferably, is an in vitro method. Moreover, it may comprise steps in addition to those explicitly mentioned above. For example, further steps may relate to sample pre-treatments or evaluation of the diagnostic data.

DETAILED DESCRIPTION OF THE INVENTION

The term "diagnosing" as used herein refers to assessing the probability according to which a subject is suffering from an acute cardiovascular event or any other disease referred to in this specification. As will be understood by those skilled in the art, such an assessment is usually not intended to be correct for 100% of the subjects to be diagnosed. The term, however, requires that a statistically significant portion of subjects can be diagnosed (e.g., a cohort in a cohort study) to suffer from heart failure or to have a risk of suffering from the disease in the future. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York, 1983. Preferred confidence intervals are at least 90%, at least 95%, at least 97%, at least 98%, or at least 99%. The p-values are, preferably, 0.1, 0.05, 0.01, 0.005, or 0.0001.

Diagnosing according to the present invention includes monitoring, confirmation, subclassification, and prediction of the relevant disease, symptoms, or risks therefor. Monitoring relates to keeping track of an already diagnosed disease or complication, e.g., to analyze the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g., defining according to mild or severe forms of the disease. Prediction relates to prognosing a disease or complication before other symptoms or markers have become evident or have become significantly altered.

The term "acute cardiovascular event" refers to all events which suddenly appear, i.e., without previous clinical signs or symptoms, and which severely affect the diastolic or systolic blood flow rate. Histopathologically, the acute cardiovascular event referred to herein shall be accompanied by a sudden ischemia of heart muscle cells accompanied by severe necrosis of said cells. Preferably, the subject suffering from an acute cardiovascular event will also suffer from typical symptoms such as chest, epigastric, arm, wrist, or jaw discomfort or pain whereby, in particular, the chest pain may radiate to the arm, back, or shoulder. Further symptoms of an acute cardiovascular event may be unexplained nausea or vomiting, persistent shortness of breath, weakness, dizziness, lightheadedness, or syncope as well as any combinations thereof.

Preferably, the acute cardiovascular event referred to herein is an acute coronary syndrome (ACS), i.e., either an unstable angina pectoris (UAP) or myocardial infarction (MI). Most preferably, the acute cardiovascular event is MI including ST-elevated MI and non-ST-elevated MI. Moreover, the cardiovascular event also encompasses stroke. Further details on the definitions, symptoms, and clinical signs such as electrocardiographic signs, are found in Joint European Society of Cardiology/American Society of Cardiology, 2000, J American College of Cardiology, Vol. 36, No. 3, 959-969. Symptoms may be classified according to the New York Heart Association classification system. Patients of class I have no obvious symptoms of cardiovascular disease. Physical activity is not limited, and ordinary physical activity does not cause undue fatigue, palpitation, or dyspnea (shortness of breath). Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased. Accordingly, patients can be divided into individuals showing no clinical symptoms and those with symptoms (e.g., dyspnea).

The term "subject" as used herein relates to animals, preferably mammals, and, more preferably, humans. However, it is envisaged by the present invention that the subject shall preferably exhibit symptoms known to be associated with an acute cardiovascular event, i.e., chest pain, dyspnea and others as described above. More preferably, the subject shall exhibit at least symptoms according to NYHA class II, most preferably, according to classes III or IV.

Determining the amount of a natriuretic peptide or a cardiac troponin according to the present invention relates to measuring the amount or concentration, preferably semi-quantitatively or quantitatively. Measuring can be done directly or indirectly. Direct measuring relates to measuring the amount or concentration of the natriuretic peptide or cardiac troponin based on a signal which is obtained from the natriuretic peptide or cardiac troponin itself and the intensity of which directly correlates with the number of molecules of the peptide present in the sample. Such a signal, sometimes referred to herein as intensity signal, may be obtained, e.g., by measuring an intensity value of a specific physical or chemical property of the natriuretic peptide or cardiac troponin. Indirect measuring includes measuring of a signal obtained from a secondary component (i.e., a component not being the natriuretic peptide itself) or a biological read out system, e.g., measurable cellular responses, ligands, labels, or enzymatic reaction products.

In accordance with the present invention, determining the amount of the natriuretic peptide or cardiac troponin can be achieved by all known means for determining the amount of a peptide in a sample. Said means comprise immunoassay devices and methods which may utilize labeled molecules in various sandwich, competition, or other assay formats. Said assays will develop a signal which is indicative for the presence or absence of the natriuretic peptide or cardiac troponin. Moreover, the signal strength can, preferably, be correlated directly or indirectly (e.g., reverse-proportional) to the amount of polypeptide present in a sample. Further, suitable methods comprise measuring a physical or chemical property specific for the natriuretic peptide such as its precise molecular mass or NMR spectrum. Said methods comprise, preferably, biosensors, optical devices coupled to immunoassays, biochips, analytical devices such as mass spectrometers, NMR analyzers, or chromatography devices. Further, methods include microplate ELISA-based methods, fully-automated or robotic immunoassays (available for example on ELECSYS analyzers, Roche Diagnostics GmbH), CBA (an enzymatic cobalt binding assay, available, for example, on Roche-Hitachi analyzers), and latex agglutination assays (available, for example, on Roche-Hitachi analyzers).

In a preferred embodiment, the method for determining the amount of a natriuretic peptide or cardiac troponin comprises the steps of (a) contacting a cell capable of eliciting a cellular response, the intensity of which is indicative of the amount of the peptide, with the peptide for an adequate period of time, (b) measuring the cellular response.

For measuring cellular responses, the sample or processed sample is, preferably, added to a cell culture, and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide.

In another preferred embodiment, the method for determining the amount of a natriuretic peptide or cardiac troponin comprises the step of measuring a specific intensity signal obtainable from the natriuretic peptide or cardiac troponin in the sample.

As described above, such a signal may be the signal intensity observed at an m/z variable specific for the natriuretic peptide or cardiac troponin observed in mass spectra or a NMR spectrum specific for the natriuretic peptide or cardiac troponin.

In another preferred embodiment, the method for determining the amount of a natriuretic peptide comprises the steps of (a) contacting the peptide with a specific ligand which bind to said peptide, (b) optionally removing non-bound ligand, and (c) measuring the amount of bound ligand.

The bound ligand will generate an intensity signal. Binding according to the present invention includes both covalent and non-covalent binding. A ligand according to the present invention can be any compound, e.g., a peptide, polypeptide, nucleic acid, or small molecule, binding to the natriuretic peptide or cardiac troponins described herein. Preferred ligands include antibodies, nucleic acids, peptides or polypeptides such as receptors for the natriuretic peptides or binding partners for the cardiac troponins and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g., phage display. Antibodies as referred to herein include both polyclonal and monoclonal antibodies, as well as fragments thereof, such as Fv, Fab, and F(ab)2 fragments that are capable of binding antigen or hapten. The present invention also includes humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the natriuretic peptide. Specific binding according to the present invention means that the ligand or agent should not bind substantially to ("cross-react" with) another peptide, polypeptide, or substance present in the sample to be analyzed. Preferably, the specifically bound natriuretic peptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a Western blot). Alternatively, the ligand may exhibit enzymatic properties itself, and the ligand/natriuretic peptide or ligand/cardiac troponin complex or the ligand which was bound by the natriuretic peptide or cardiac troponin, respectively, may be contacted with a suitable substrate, allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary, or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxigenin, His-Tag, glutathione-S-transferase, FLAG, GFP (green fluorescent protein), myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., "magnetic beads", including paramagnetic and superparamagnetic labels), and fluorescent labels. Enzymatically active labels include, e.g., horseradish peroxidase, alkaline phosphatase, beta-galactosidase, luciferase, and derivatives thereof. Suitable substrates for detection include diaminobenzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence, or chemiluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include 35S, 125I, 32P, 33P, and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western blotting, and mass spectrometry), can be used alone or in combination with labeling or other detection methods as described above.

In another preferred embodiment, the method for determining the amount of a natriuretic peptide comprises (a) contacting a solid support comprising a ligand for the natriuretic peptide or cardiac troponin as specified above with a sample comprising the natriuretic peptide or cardiac troponin and (b) measuring the amount of natriuretic peptide or cardiac troponin which is bound to the support.

The ligand, preferably chosen from the group consisting of nucleic acids, peptides, polypeptides, antibodies, and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells, and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions, and the like. It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g., a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of the natriuretic peptides or cardiac troponins, the relative amount or concentration of the natriuretic peptides or cardiac troponins, as well as any value or parameter which correlates thereto. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., expression levels determined from biological read out systems in response to the peptides or intensity signals obtained from specifically bound ligands. It is to be understood that values correlating to the aforementioned amounts or parameters can also be obtained by all standard mathematical operations.

The term "cardiac troponin" refers to all troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493.

Preferably, cardiac troponin refers to troponin T and/or troponin I.

Accordingly, both troponins may be determined in the method of the present invention together, i.e., simultaneously or sequentially, or individually, i.e., without determining the other isoform at all.

Amino acid sequences for human troponin T and human troponin I are disclosed in Anderson, loc cit and Ferrieres 1998, Clinical Chemistry, 44: 487-493. The term "cardiac troponin" encompasses also variants of the aforementioned specific troponins, i.e., preferably, of troponin T or troponin I. Such variants have at least the same essential biological and immunological properties as the specific cardiac troponins. In particular, they share the same essential biological and immunological properties if they are detectable by the same specific assays referred to in this specification, e.g., by ELISA assays using polyclonal or monoclonal antibodies specifically recognizing the cardiac troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific troponin. Variants may be allelic variants or any other species specific homologs, paralogs, or orthologs. Moreover, the variants referred to herein include fragments of the specific cardiac troponins or the aforementioned types of variants as long as these fragments have the essential immunological and biological properties as referred to above. Such fragments may be, e.g., degradation products of the troponins. Further included are variants which differ due to posttranslational modifications such as phosphorylation or myristylation.

The term "natriuretic peptide" comprises atrial natriuretic peptide (ANP)-type and brain natriuretic peptide (BNP)-type peptides and variants thereof having the same predictive potential. Natriuretic peptides according to the present invention comprise ANP-type and BNP-type peptides and variants thereof (see, e.g., Bonow, R. O. (1996). New insights into the cardiac natriuretic peptides. Circulation 93: 1946-1950).

ANP-type peptides comprise pre-proANP, proANP, NT-proANP, and ANP.

BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolized in the blood, whereas NT-proBNP circulates in the blood as an intact molecule and as such is eliminated renally.

The in vivo half-life of NT-proBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J. Endocrinol. 2000; 167: 239-46.).

Preanalytics are more robust with NT-proBNP, allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° C. leads to a concentration loss of at least 20% (Mueller T, Gegenhuber A, et al., Clin Chem Lab Med 2004; 42: 942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.). Therefore, depending on the time-course or properties of interest, either measurement of the active or the inactive forms of the natriuretic peptide can be advantageous.

The most preferred natriuretic peptides according to the present invention are NT-proBNP or variants thereof. As briefly discussed above, the human NT-proBNP as referred to in accordance with the present invention is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, and Bonow 1996, New Insights into the cardiac natriuretic peptides. Circulation 93: 1946-1950. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein.

The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are immunological and/or biological properties. Preferably, the NT-proBNP variants have immunological properties (i.e., epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999. Development of a novel, N-Terminal-proBNP (NT-proBNP) assay with a low detection limit. Scand J Clin Invest 59:177-181), Yeo et al. (Yeo 2003. Multicenter evaluation of the Roche NT-proBNP assay and comparison to the Biosite Triage assay. Clinica Chimica Acta 338:107-115), and in Example 1, below. Variants also include posttranslationally modified peptides such as glycosylated peptides.

A variant in accordance with the present invention is also a peptide or polypeptide which has been modified after collection of the sample, for example, by covalent or non-covalent attachment of a label, particularly a radioactive or fluorescent label, to the peptide.

The term "sample" refers to a sample of a body fluid, to a sample of separated cells, or to a sample from a tissue or an organ. Samples of body fluids can be obtained by well known techniques and include, preferably, samples of blood, plasma, serum, or urine. Tissue or organ samples may be obtained from any tissue or organ by, e.g., biopsy. Separated cells may be obtained from the body fluids or the tissues or organs by separating techniques such as centrifugation or cell sorting. Preferably, cell, tissue or organ samples are obtained from those cells, tissues, or organs which express or produce the peptides referred to herein (i.e., the natriuretic peptides and the cardiac troponins.

"Comparing" as used herein encompasses comparing the amount of the natriuretic peptide or cardiac troponin comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in the method of the present invention may be carried out manually or computer assisted. For a computer assisted comparison, the value of the determined amount may be compared to values corresponding to suitable references which are stored in a database by a computer program. The computer program may further evaluate the result of the comparison, i.e., automatically provide the desired diagnosis in a suitable output format.

The term "reference amount" as used herein refers to an amount which allows assessing whether a subject will suffer from an acute cardiovascular event or another disease referred to in this specification by a comparison as referred to above. Accordingly, the reference may either be derived from a subject suffering from an acute cardiovascular event or a subject being healthy at least with respect to acute cardiovascular events. The reference amount applicable for an individual subject may vary depending on various physiological parameters such as age, gender, or subpopulation. Thus, a suitable reference amount may be determined by the method of the present invention from a reference sample to be analyzed together, i.e., simultaneously or subsequently, with the test sample. In principle, it has been found in accordance with the present invention that during progression of chronic heart failure, the amount of cardiac troponins to be found, e.g., in plasma will also increase. Moreover, as chronic heart failure becomes more severe, the amount of natriuretic peptides in the plasma will become higher. Thus, with respect to a healthy subject, elevated plasma cardiac troponin and natriuretic peptide amounts shall be associated with a higher probability of suffering from chronic heart failure. On the other hand, an elevation, merely, of the amount of the plasma cardiac troponins shall be associated with a higher risk for suffering from an acute cardiovascular event. More preferably, it has been round in accordance with the present invention that a reference amount for the cardiac troponin of at least 0.01 ng/ml and a reference amount of the natriuretic peptide less than 500 pg/ml are indicative for an acute cardiovascular event. Moreover, a reference amount of the cardiac troponin of at least 3.5 ng/ml and a reference amount for the natriuretic peptide of at least 500 pg/ml is also indicative for (i.e., associated with a higher-probability for developing) an acute cardiovascular event.

Surprisingly, it has been found in the studies underlying the present invention that false positive findings relating to the diagnosis of an acute cardiovascular event may be avoided by taking into account two biochemical markers, i.e., a cardiac troponin and a natriuretic peptide, rather than the current gold standard marker troponin T, solely. Advantageously, subjects suffering from an acute cardiovascular event can be reliably diagnosed and distinguished from subjects suffering from other disorders. It is to be understood that the subjects will greatly benefit from this more reliable diagnosis since specific and effective therapies may be readily applied.

The definitions and explanations of the terms made above and below apply accordingly for all embodiments described in this specification and the accompanying claims.

It follows from the above that in a particularly preferred embodiment of the method of the present invention, (i) a reference amount for cardiac troponin of at least 0.01 ng/ml and a reference amount of natriuretic peptide less than 500 pg/ml or (ii) a reference amount for cardiac troponin of at least 3.5 ng/ml and reference amount for natriuretic peptide of at least 500 pg/ml are indicative for an acute cardiovascular event.

Further, the present invention relates to a method for differentiating between an acute cardiovascular event and chronic heart failure comprising the steps of:

a) determining the amount of a cardiac troponin in a sample of a subject;

b) determining the amount of a natriuretic peptide in a sample of said subject, and c) differentiating between an acute cardiovascular event and chronic heart failure by comparing the amounts determined in step a) and b) with reference amounts.

The term "differentiating" as used herein means to distinguish between a subject which suffers from an acute cardiovascular event and a subject suffering from chronic heart failure even under conditions where the subjects show essentially the same clinical signs and symptoms and are both positive for an acute cardiovascular event in the currently applied troponin T test. The term as used herein, preferably, includes diagnosing either an acute cardiovascular event or chronic heart failure or both diseases together as referred to in this specification.

The term "chronic heart failure" as used herein refers to chronic, i.e., permanent, heart failure. Heart failure is characterized by an impaired diastolic or systolic blood flow rate and, thus, by an impaired function of the heart. However, rather than exhibiting sudden ischemia accompanied by severe necrosis of the heart muscle cells, chronic heart failure as referred to herein is, preferably, accompanied by continuous necrotic events in heart muscle cells which result in a continuously developing impaired function of the heart.

Advantageously, the present invention, by providing the aforementioned method for differentially diagnosing an acute cardiovascular event and a chronic heart failure, allows to reliably and time- as well as cost-effectively distinguish between said disease conditions. Therefore, subjects suffering from the said diseases can be readily treated by specific and effective therapies rather than unspecific and ineffective therapies.

Specifically preferred embodiments of the method of the present invention are referred to as follows:

In a preferred embodiment of the method of the present invention, a reference amount for the cardiac troponin between and including 0.01 ng/ml and 3.5 ng/ml and a reference amount for the natriuretic peptide of at least 500 pg/ml are indicative for chronic heart failure.

In another preferred embodiment of the method of the present invention, (i) a reference amount for the cardiac troponin of at least 0.01 ng/ml and a reference amount of the natriuretic peptide less than 500 pg/ml or (ii) a reference amount for the cardiac troponin of greater than 3.5 ng/ml and a reference amount for the natriuretic peptide of at least 500 pg/ml are indicative for an acute cardiovascular event.

In a preferred embodiment of the method of the present invention, the natriuretic peptide is BNP, more preferably, NT-proBNP.

In a further preferred embodiment of the method of the present invention, the natriuretic peptide is ANP, more preferably, NT-proANP.

In a furthermore preferred embodiment of the method of the present invention, said cardiac troponin is troponin T and/or troponin I.

Also, in a preferred embodiment of the method of the present invention, said subject is a human.

The present invention further relates to a device for diagnosing an acute cardiovascular event comprising:
 a) means for determining the amount of a cardiac troponin in a sample of a subject;
 b) means for determining the amount of a natriuretic peptide in a sample; and
 c) means for comparing said amounts to a suitable reference, whereby an acute cardiovascular event is diagnosed.

The term "device" as used herein relates to a system of means comprising at least the aforementioned means operatively linked to each other as to allow the prediction. Preferred means for determining the amount of the natriuretic peptides or cardiac troponins and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose an acute cardiovascular event or other disease referred to herein. Preferably, the means are comprised by a single device in such a case. Said device may include an analyzing unit for the measurement of the amount of the peptides in a sample and a computer unit for processing the resulting data for the differential diagnosis. Alternatively, where means such as test strips are used for determining the amount of the peptides, the means for diagnosing may comprise control strips or tables allocating the determined amount to an amount known to be accompanied with an acute cardiovascular event or other diseases referred to herein or an amount known to be indicative for a healthy subject. The test strips are, preferably, coupled to a ligand which specifically binds to the natriuretic peptide or cardiac troponin. The strip or device, preferably, comprises means for detection of the binding of said peptides to the ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of diagnostic raw data which need interpretation by the clinician. Preferably, the output of the device are, however, processed diagnostic raw data, the interpretation of which does not require a clinician, i.e., it should be inevitably clear from the output whether the subject suffers from mild or moderate heart failure. Further preferred devices comprise the analyzing units/devices (e.g., biosensors, arrays, solid supports coupled to ligands specifically recognizing the natriuretic peptide, plasmon surface resonance devices, NMR spectrometers, mass spectrometers etc.) or evaluation units/devices referred to above in accordance with the method of the invention.

Moreover, encompassed by the present invention is also a device for differentiating between an acute cardiovascular event and heart failure comprising:
 a) means for determining the amount of a cardiac troponin in a sample of a subject;
 b) means for determining the amount of a natriuretic peptide in a sample; and
 c) means for comparing said amounts to a suitable reference, whereby it is differentiated between an acute cardiovascular event and chronic heart failure.

Finally, the present invention relates to a kit for carrying out the method of the present invention comprising:
 a) means for determining the amount of a cardiac troponin in a sample of a subject,
 b) means for determining the amount of a natriuretic peptide in a sample; and
 c) means for comparing said amounts to a suitable reference, whereby it is differentiated between an acute cardiovascular event and chronic heart failure.

The term "kit" as used herein refers to a collection of the aforementioned means, preferably, provided separately or within a single container. The container, also preferably, comprises instructions for carrying out the method of the present invention.

All references cited in this specification are herewith incorporated by reference with respect to their entire disclosure content and the disclosure content specifically mentioned in this specification.

The following examples shall merely illustrate the invention. They shall not be construed, whatsoever, to limit the scope of the invention.

SPECIFIC EMBODIMENTS

Example 1

Case Study

In a case study, 12 patients have been confirmed to suffer from an acute coronary syndrome according to the method of the present invention. All patients have been investigated after showing the symptoms of an acute cardiovascular event by an initial troponin T test and later, by a high-sensitivity troponin T test. The results are shown in the accompanying Table 1.

As is evident from the table, all patients are positive for troponin T by using the high-sensitivity assay. Moreover, the NT-proBNP values of the patients are also shown. In the last column the final diagnosis is indicated. The data shown for 12 patients in the accompanying table demonstrate that troponin T as well as NT-proBNP values may be used in combination to diagnose an acute coronary syndrome, such as ST elevation or non-ST elevation myocardial infection (STEMI or NSTEMI).

TABLE 1

N = 12 ACS Patients developed TnT positive

| Patient-No. | Time Interval Hours | TnT Class | TnT Value Ng/ml | hs-TnT pg/ml | NT-proBNP pg/ml | Final Diagnosis |
|---|---|---|---|---|---|---|
| 1 | 0 | Negativ | | 1.806 | 30.927 | NSTEMI |
| 1 | 4 | Positiv | 0.06 | 20.325 | 23.022 | NSTEMI |
| 2 | 0 | Negativ | | 22.032 | 305.446 | STEMI |
| 2 | 3 | Positiv | 0.42 | 481.413 | 354.206 | STEMI |
| 3 | 0 | Negativ | | 11.582 | 247.036 | STEMI |
| 3 | 3 | Positiv | 0.28 | 230.721 | 340.736 | STEMI |
| 4 | 0 | Negativ | | 2.896 | 139.132 | STEMI |
| 4 | 2 | Positiv | 1.62 | 972.338 | 170.695 | STEMI |
| 5 | 0 | Negativ | | 27.905 | 288.439 | STEMI |
| 5 | 3 | Positiv | 0.06 | 70.888 | 219.762 | STEMI |
| 6 | 0 | Negativ | | 28.832 | 29.493 | STEMI |
| 6 | 2 | Positiv | 1.26 | 1226.998 | 33.311 | STEMI |
| 7 | 0 | Negativ | | 21.806 | 210.089 | NSTEMI |
| 7 | 4 | Positiv | 0.08 | 83.659 | 267.730 | NSTEMI |
| 8 | 0 | Negativ | | 20.513 | 66.194 | STEMI |
| 8 | 1 | Positiv | 0.54 | 585.033 | 69.231 | STEMI |
| 9 | 0 | Negativ | | 28.975 | 115.515 | STEMI |
| 9 | 2 | Positiv | 0.05 | 62.535 | 134.740 | STEMI |
| 10 | 0 | Negativ | | 20.211 | 19.441 | NSTEMI |
| 10 | 3 | Positiv | 0.04 | 46.179 | 27.701 | NSTEMI |
| 11 | 0 | Negativ | | 2.235 | 19.734 | STEMI |
| 11 | 4 | Positiv | 1.90 | 1416.137 | 34.835 | STEMI |
| 12 | 0 | Negativ | | 10.100 | 72.550 | NSTEMI |
| 12 | 3 | Positiv | 0.20 | 168.907 | 62.872 | NSTEMI |

Example 2

Case Study

For a cohort of 73 patients suffering from an acute cardiovascular event with a prior known heart failure, NT-proBNP, BNP, NT-proANP as well as troponin T has been measured. The measurement has been carried out at the time-point when the patients arrived at the emergency hospital and subsequently after 12 hours and after 24 hours. Patients which showed no elevation of the troponin T amount between the aforementioned time-points of measurement have been deemed to exhibit chronic necrosis. These patients have been sub-divided into groups according to the following criteria: troponin T below the detection level, troponin T above the detection level, however, below the clinical cut-off of 0.1 ng/ml and troponin T above the clinical cut-off value of 0.1 ng/ml. As is evident from Table 2, an elevated troponin T value is accompanied with significantly elevated BNP, NT-proBNP, and NT-proANP amounts. It should be noted that a continuous troponin T elevation above a value of 3 ng/ml appears rarely.

TABLE 2

Chronic Heart Failure Patients classified in TnT Categories at Time Point 0

| | Troponin T Category | | |
|---|---|---|---|
| | <0.01 ng/ml | 0.01-0.1 ng/ml | >0.1 ng/ml |
| N | 16 | 18 | 25 |
| N death (%) | 1 (6%) | 5 (28%) | 11 (44%) |
| NT-proBNP [pg/ml] | | | |
| Min | 400 | 2403 | 934 |
| Median | 4129 | 5945 | 8232 |
| Max | 13585 | 79998 | 26791 |
| NT-proANP [pg/ml] | | | |
| Min | 2657 | 4137 | 3716 |
| Median | 9764 | 14741 | 17580 |
| Max | 18650 | 39053 | 52584 |
| BNP [pg/ml] | | | |
| Min | 47.3 | 276 | 43.9 |
| Median | 399 | 784 | 615 |
| Max | 206 | 3548 | 2706 |
| proANP/proBNP Ratio | | | |
| Min | 0.54 | 0.33 | 0.6 |
| Median | 2.38 | 1.62 | 2.38 |
| Max | 8.44 | 4.45 | 9.31 |

Example 3

Case Study

In a further cohort of patients (n=235) suffering from coronary heart disease, NT-proBNP and troponin T has been investigated. The patients did not suffer from an acute cardiovascular event, i.e., the last acute cardiovascular event appeared at least one week ago. The patients were grouped as described in Example 2 above. The results of the study are shown in Table 3 below.

TABLE 3

High-sensitive troponin T categories in patients with documented coronary artery disease

| | Hs-TnT [ng/ml] N = 235 Diagnosis Group 1 | | |
|---|---|---|---|
| | 0.0-0.0010 | 0.00105-0.100 | >0.100 |
| N | 140 | 75 | 20 |
| Median | 0.0021 | 0.024 | 0.1645 |
| Range | 0.0-0.0010 | 0.00105-0.0994 | 0.101-0.708 |
| Age, median | 65 | 69 | 69 |
| Male (n) | 85 | 49 | 17 |
| Female (n) | 55 | 26 | 3 |
| BMI, median kg/m2 | 27.8 | 27.3 | 26.7 |
| N LVEF (%) | | | |
| >60% | 119 | 37 | 8 |

TABLE 3-continued

High-sensitive troponin T categories in patients with documented coronary artery disease

| | Hs-TnT [ng/ml] N = 235 Diagnosis Group 1 | | |
|---|---|---|---|
| | 0.0-0.0010 | 0.00105-0.100 | >0.100 |
| 40-60% | 6 | 12 | 5 |
| <40% | 15 | 26 | 7 |
| LA (mm), median | 40.0 | 42.0 | 40.0 |
| SEP (mm), median | 12.0 | 12.0 | 12.0 |
| Coronary Artery Disease | | | |
| 1- vessel disease | 24 | 14 | 2 |
| 2-vessel disease | 33 | 14 | 3 |
| 3-vessel disease. | 37 | 31 | 8 |
| Smoker (n) | 66 | 38 | 11 |
| Diabetes (n) | 32 | 29 | 6 |
| Art. Hypertension (n) | 99 | 55 | 10 |
| Heart Rate | 66 | 74 | 68 |
| Previous MI (n) | 38 | 31 | 16 |
| Median Cholesterol mg/dl | 228.0 | 217.0 | 222.5 |
| Median LDL mg/dl | 148.8 | 137.8 | 154.9 |
| Median Triglycerides mg/dl | 161.0 | 151.0 | 142.0 |
| NT-proBNP pg/ml | | | |
| perc(0) | 5.000 | 11.200 | 158.700 |
| perc(2.5) | 14.450 | 31.000 | 159.100 |
| perc(5) | 21.600 | 53.650 | 159.100 |
| perc(10) | 31.150 | 84.450 | 200.300 |
| perc(25) | 58.750 | 278.350 | 293.950 |
| perc(50); Median | 141.200 | 719.400 | 870.100 |
| perc(75) | 292.000 | 2171.500 | 2697.000 |
| perc(90) | 806.100 | 4200.500 | 3835.000 |
| Perc(95) | 1261.000 | 7068.500 | 6651.500 |
| Perc(97.5) | 2279.500 | 11582.500 | 6651.500 |
| perc(100) | 5774.000 | 14953.000 | 9298.000 |
| NT-proANP pg/ml | | | |
| perc(0) | 901.042 | 1185.028 | 1525.110 |
| perc(2.5) | 1102.637 | 1256.901 | 1570.688 |
| perc(5) | 1190.287 | 1602.242 | 1570.688 |
| perc(10) | 1279.690 | 1859.933 | 1691.645 |
| perc(25) | 1646.067 | 2771.493 | 2007.185 |
| perc(50); Median | 2331.490 | 4277.320 | 3204.484 |
| perc(75) | 3053.726 | 7029.530 | 5890.080 |
| perc(90) | 4943.460 | 10219.990 | 6626.340 |
| perc(95) | 5907.610 | 12972.200 | 6889.290 |
| Perc(97.5) | 6678.930 | 16758.680 | 6889.290 |
| perc(100) | 9536.320 | 27977.880 | 7082.120 |
| proANP/proBNP Ratio | | | |
| perc(0) | 0.308 | 0.599 | 0.720 |
| perc(5) | 1.935 | 0.926 | 1.004 |
| perc(10) | 2.831 | 1.443 | 1.401 |
| perc(25) | 7.276 | 2.644 | 1.896 |
| perc(50); Median | 15.950 | 5.293 | 2.697 |
| perc(75) | 31.948 | 10.973 | 7.487 |
| perc(90) | 55.549 | 39.271 | 12.610 |
| perc(95) | 75.845 | 77.594 | 17.245 |
| Perc(97.5) | 97.744 | 183.260 | 17.245 |
| perc(100) | 244.018 | 369.785 | 21.058 |

What is claimed is:

1. A method for differentiating between an acute cardiovascular event and chronic heart failure comprising the steps of:
   a. determining an amount of a cardiac troponin in a sample from a human subject,
   b. determining an amount of a natriuretic peptide in a sample from said subject, and
   c. differentiating between an acute cardiovascular event and chronic heart failure by comparing the amounts determined in steps a) and b) with reference amounts,
   wherein a reference amount for the cardiac troponin between and including 0.01 ng/ml and 3.5 ng/ml and a reference amount for the natriuretic peptide of at least 500 pg/ml are indicative for chronic heart failure, and
   wherein a reference amount for the cardiac troponin of greater than 0.01 ng/ml and a reference amount for the natriuretic peptide of less than 500 pg/ml are indicative for an acute cardiovascular event or wherein a reference amount for the cardiac trononin of at least 3.5 ng/ml and a reference amount of the natriuretic peptide of at least 500 pg/ml are indicative for an acute cardiovascular event.

2. The method of claim 1 wherein the natriuretic peptide is brain natriuretic peptide (BNP).

3. The method of claim 2 wherein the BNP is N-terminal pro-brain natriuretic peptide (NT-proBNP).

4. The method of claim 1 wherein the natriuretic peptide is atrial natriuretic peptide (ANP).

5. The method of claim 4 wherein the ANP is N-terminal pro-atrial natriuretic peptide (NT-proANP).

6. The method of claim 1 wherein said cardiac troponin is troponin T or troponin I.

7. A method for diagnosing an acute cardiovascular event comprising the steps of:
   a. determining an amount of a cardiac troponin in a sample from a human subject,
   b. determining an amount of a natriuretic peptide in a sample from said subject, and
   c. diagnosing an acute cardiovascular event by comparing the amounts determined in steps a) and b) with reference amounts,
   wherein a reference amount for the cardiac troponin of at least 0.01 ng/ml and a reference amount for the natriuretic peptide of less than 500 pg/ml are indicative for an acute cardiovascular event or wherein a reference amount for the cardiac troponin of at least 3.5 ng/ml and a reference amount of the natriuretic peptide of at least 500 pg/ml are indicative for an acute cardiovascular event.

8. The method of claim 7 wherein the natriuretic peptide is brain natriuretic peptide (BNP).

9. The method of claim 8 wherein the BNP is N-terminal pro-brain natriuretic peptide (NT-proBNP).

10. The method of claim 7 wherein the natriuretic peptide is atrial natriuretic peptide (ANP).

11. The method of claim 10 wherein the ANP is N-terminal pro-atrial natriuretic peptide (NT-proANP).

12. The method of claim 7 wherein the cardiac troponin is troponin T or troponin I.

* * * * *